United States Patent
Franck et al.

(10) Patent No.: US 12,426,792 B2
(45) Date of Patent: Sep. 30, 2025

(54) PROCESSING UNIT AND METHOD FOR USE IN FETAL MONITORING

(71) Applicant: KONINKLIJKE PHILIPS N.V., Eindhoven (NL)

(72) Inventors: Christoph Florian Franck, Magstadt (DE); Markus Silvester Wohlschlager, Sindelfingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 483 days.

(21) Appl. No.: 17/911,471

(22) PCT Filed: Mar. 16, 2021

(86) PCT No.: PCT/EP2021/056580
§ 371 (c)(1),
(2) Date: Sep. 14, 2022

(87) PCT Pub. No.: WO2021/185787
PCT Pub. Date: Sep. 23, 2021

(65) Prior Publication Data
US 2023/0090637 A1 Mar. 23, 2023

(30) Foreign Application Priority Data
Mar. 16, 2020 (EP) .................... 20163244

(51) Int. Cl.
*A61B 5/02* (2006.01)
*A61B 5/00* (2006.01)
(Continued)

(52) U.S. Cl.
CPC .......... *A61B 5/02411* (2013.01); *A61B 5/339* (2021.01); *A61B 5/344* (2021.01); *A61B 5/4362* (2013.01)

(58) Field of Classification Search
CPC ... A61B 5/0011; A61B 5/02411; A61B 5/339; A61B 5/344; A61B 5/4362
See application file for complete search history.

(56) References Cited

U.S. PATENT DOCUMENTS

| 3,991,365 A | 11/1976 | Takeuchi |
| 7,519,417 B2 | 4/2009 | Ferguson |

(Continued)

FOREIGN PATENT DOCUMENTS

| EP | 3155963 A1 | 4/2017 |
| GB | 2482758 A | 2/2012 |

OTHER PUBLICATIONS

Rik Vullings, "Non-invasive fetal electrocardiogram: analysis and interpretation" Chapter 5.

(Continued)

*Primary Examiner* — Amanda K Hulbert

(57) ABSTRACT

A device and method for deriving and displaying a time-averaged fetal heart rate signal in conjunction with micro-variability information relating to variation in the beat-to-beat heart rate signal within the different time-averaging epochs or windows. Supplementary information is displayed, for example temporally aligned or registered with the time-average heart rate signal, which is indicative of variation information for the signal during averaging windows of the time-averaged signal.

14 Claims, 2 Drawing Sheets

(51) Int. Cl.
    *A61B 5/024*      (2006.01)
    *A61B 5/339*      (2021.01)
    *A61B 5/344*      (2021.01)

(56) References Cited

U.S. PATENT DOCUMENTS

| | | | |
|---|---|---|---|
| 8,396,540 | B2 | 3/2013 | Miller |
| 2004/0133115 | A1 | 7/2004 | Hamilton |
| 2008/0045849 | A1 | 2/2008 | Outram |
| 2010/0191135 | A1 | 7/2010 | Kuo |
| 2012/0150010 | A1 | 6/2012 | Hayes-Gill |
| 2014/0378855 | A1* | 12/2014 | Dash .............. A61B 5/02411 600/511 |

OTHER PUBLICATIONS

Hasan et al, "Detection and Processing Techniques of FECG Signal for Fetal Monitoring".

International Search Report dated May 28, 2021 for International Appln No. PCT/EP2021/056580 filed Mar. 16, 2021.

V.M. Roemer, R. Walden, "The Factor Time in Fetal Heart Rate Monitoring and the Detection of Acidosis Using the WAS Score", Z Geburtshilfe Neonatol 2014; 218(02): 80-86. DOI: 10.1055/s-0034-1372596.

V.M. Roemer, R. Walden, "Fetal Heart Rate Patterns during Delivery Complicated by Hypoxia and Acidosis—A Computer-Aided Analysis", Z Geburtshilfe Neonatol 2013; 217(01): 28-34. DOI: 10.1055/s-0032-1331742.

V.M. Roemer, R. Walden, "Basic Principles of the Foetal Heart Rate during Delivery without Hypoxia and Acidosis", Z Geburtshilfe Neonatol 2012; 216(01): 11-21. DOI: 10.1055/s-0031-1291340.

V. M. Roemer, "Was ist ein pathologisches" CTG ? How to Define a Non-Reassuring FHR Tracing Online, Z Geburtshilfe Neonatol 2010; 214(4): 151-160. DOI: 10.1055/s-0030-1261962.

V. M. Roemer, R. Walden, "Sensitivity, Specificity, Receiver-Operating Characteristic (ROC) Curves and Likelihood Ratios for Electronic Foetal Heart Rate Monitoring using New Evaluation Techniques", Z Geburtshilfe Neonatol 2010; 214(3): 108-118. DOI: 10.1055/s-0030-1255022.

V. M. Roemer, R. Walden, "Ein neuer Weg zur quantitativen elektronischen CTG-Analyse. A New Approach to Quantitative Electronic Foetal Heart-Rate Analysis", V. M. Roemer, R. Walden, Z Geburtshilfe Neonatol 2010; 214(1):1-10. DOI: 10.1055/s-0029-1243163.

V. M. Roemer, "CTG: Mikrofluktuation. Fetal heart frequency: Microfluctuation", Z Geburtshilfe Neonatol 2004; 208(6): 210-219. DOI: 10.1055/s-2004-835867.

* cited by examiner

PROCESSING UNIT AND METHOD FOR USE IN FETAL MONITORING

CROSS-REFERENCE TO PRIOR APPLICATIONS

This application is the U.S. National Phase application under 35 U.S.C. § 371 of International Application No. PCT/EP2021/056580, filed on Mar. 16, 2021, which claims the benefit of European Application No. 20163244.5 filed on Mar. 16, 2020. These applications are hereby incorporated by reference herein.

FIELD OF THE INVENTION

The present invention relates to a processing unit and method for deriving and presenting information related to a fetal heart from sensor data.

BACKGROUND OF THE INVENTION

Electronic fetal monitoring (EFM) comprises methods for recording vital parameters, such as heart rate, of a fetus in utero during pregnancy and labor.

The most common EFM methods include cardiotocograhy, comprising monitoring fetal heart rate (FHR) using ultrasound, and fetal electrocardiography (fECG), which comprises use of ECG measurement technology. For fECG, this can be done either by attaching an electrode to the fetal scalp during later stages of labor or by attaching electrodes to the maternal abdomen and recovering the fetal ECG signal electronically or digitally.

EFM measurements can be used, inter alia, to assess the health, metabolic condition and oxygen supply of the fetus. This information can be used to inform therapeutic decisions, e.g. for determining whether delivery by Cesarean section is medically necessary to prevent damage to the fetus from hypoxia.

Improving the quality of the information provided by an EFM system can thus improve medical outcomes for patients, as well as helping reduce the rate of unnecessary Cesarean sections.

Current EFM systems typically output measurement information in the form of a graph of the fetal heart rate over a time range of minutes to hours. Each recorded heart rate data point is usually an average of several beat-to-beat heart rate values over an averaging period of several seconds. This makes the graph easier to read by smoothing over very short-term fluctuations. However, it necessarily also discards some of the information that would be contained in a true beat-to-beat heart rate recording. This type of information is usually referred to as FHR microvariability or microfluctuations.

The microvariability information can be a useful clinical parameter since for example high inter-beat heart rate variability or low variability can be indicative of different clinically significant states of the fetus. However, simply displaying the full non-smoothed inter-beat heart rate would then impede normal interpretation of heart rate, due to the high level of fluctuation. Also, it is not desirable to change the standard the representation of the fetal heart rate since this would then look unfamiliar to a clinician, making it difficult for them to quickly apply their previous experience in interpreting the graph for rapid decision making.

Thus an improved EFM system capable of overcoming one or more of the above problems would be of value.

Electronic fetal monitoring (EFM) typically uses Doppler ultrasound to acquire a pulse (heart rate) signal from a fetus in utero during pregnancy and labor. The fetal heart rate (FHR) is calculated using the acquired pulse signal.

SUMMARY OF THE INVENTION

The invention is defined by the claims.

According to examples in accordance with an aspect of the invention, there is provided a processing unit, for use in fetal heart rate monitoring, the processing unit configured to:
receive physical sensor data containing information indicative of fetal heart activity and process the sensor data to derive a fetal heart rate signal;
derive a moving time-average signal from the fetal heart rate signal, with a time averaging window of a defined duration;
derive supplementary information for supplementing the time-averaged signal additional information about fetal heart rate microvariability based on local variation of the heart rate signal during each averaging window of the moving time-average signal;
generate a display output for provision to a display device, the display output for simultaneous display of: a graphic representation of a signal trace of the moving time-average heart rate signal, and a graphic representation of the supplementary information.

Embodiments of the present invention are based on deriving a beat-to-beat fetal heart rate signal containing the microvariability information and then generating a display output which includes a smoothed (time-averaged) heart rate signal (in accordance with standard modes of presentation for the heart rate) and further including simultaneous display of information relating to variation of the signal during each averaging time window (i.e. of the microvariability information).

Embodiments thus provide a system or method for supplementing a (for example long-term) time-averaged FHR graph with additional information about FHR microvariability, while substantially retaining the appearance of the standard (time-averaged) FHR graph that someone who is familiar with EFM systems is used to.

This is by virtue of presenting the information lost from the beat-to-beat FHR signal when deriving the time-smoothed signal, in the form of supplemental intra-epoch variability information which can, in preferred embodiments, accordingly be plotted in concert with the fetal heart rate signal itself, for example in parallel along the same time axis.

The fetal heart rate signal means for example a signal indicative of the heart rate of the fetus as a function of time.

The derived fetal heart rate signal is preferably a beat-to-beat fetal heart rate signal.

The supplementary information is preferably indicative of beat-to-beat variability in the heart rate.

The supplementary information is displayed graphically, making it more intuitive to interpret.

By displaying the supplementary information simultaneously with the time-averaged heart rate signal, but as a separate graphic representation, this ensures that the microvariability information is presented spatially in concert or conjunction with the corresponding heart rate signal (enabling the two to be read and interpreted together, in the same context), while at the same time ensuring natural interpretation of the standard time-averaged heart rate signal by a clinician is not impeded.

In examples, the supplementary information may be provided superposed on or adjacent to, the graphic representation of the fetal heart rate signal.

The supplementary information may be provided displayed in temporal registration or alignment with the time-averaged heart rate signal, i.e. each supplementary data point or information point temporally aligned with the corresponding time averaging window of the time-averaged signal to which it corresponds.

The fetal heart rate signal may in examples be displayed as a graph having axes, the axes defining a graph area, and wherein supplementary information is displayed within said same graph area. For example, the supplementary information may be represented in the form of one or more signal traces plotted on the same time axis as the time-average heart rate signal. This way, the supplementary information can be provided in temporal registration or alignment with the time-averaged heart rate signal, meaning the two can be easily interpreted together, in conjunction.

In some examples, the one or more signal traces may be spatially offset from the time-average heart rate signal, and optionally displayed with a different line style to the time-average heart rate signal. For example, they may be positioned above or below the time-averaged signal for example.

A different line style means, by way of non-limiting example, a different line thickness, line boldness, line color, line dash style (or continuous line).

In accordance with one or more embodiments, the supplementary information may include a minimum and/or maximum fetal heart rate during each averaging window.

According to one or more embodiments, the supplementary information may include a first and second signal trace representative respectively of a minimum fetal heart rate and maximum fetal heart rate during each averaging period, the signal traces displayed below and above the time average signal respectively, plotted on the same time axis as the time average signal.

According to one or more advantageous embodiments, the area between the time average signal and each of the signal traces for the maximum and minimum heart rate values may be provided at least partially shaded or colored. By thus providing the areas between the maximum and minimum lines filled or shaded or highlighted, this provides a highly intuitive integrated representation of the supplementary and time-averaged heart rate information in a way that allows them both to be read and understood in conjunction.

In accordance with one or more further embodiments, the representation of the supplementary information may comprise periodically spaced box plots rendered at successive points along the time-average heart rate signal. They may be rendered at points temporally aligned with the particular temporal averaging window to which they correspond for example.

The supplementary information may further include for each of the averaging windows an interquartile range for the heart rate, percentile ranges for the heart rate, and/or a standard deviation of the heart rate (over the averaging period).

In accordance with one or more sets of embodiments, the physical sensor data may be ultrasound data, and preferably Doppler ultrasound data.

Examples in accordance with a further aspect of the invention provide a system comprising:
  a processing unit in accordance with any example or embodiment outlined above or described below, or in accordance with any claim of this application; and
  a display device operatively coupled with the processing unit for receiving the display output.

The system may further comprise one or more physical sensors operatively coupled to the processor unit for supplying the physical sensor data, for example one or more ultrasound transducer units.

Examples in accordance with a further aspect of the invention provide a processing method for use in fetal heart rate monitoring, comprising:
  receiving physical sensor data containing information indicative of fetal heart activity and process the sensor data to derive a fetal heart rate signal;
  deriving a moving time-average signal from the fetal heart rate signal, with a time averaging window of a defined duration;
  deriving supplementary information for supplementing the moving time-averaged signal additional information about fetal heart rate microvariability based on local variation of the fetal heart rate signal during each averaging window of the moving time-average signal; and
  generating a display output for provision to a display device, the display output for simultaneous display of:
    a graphic representation of the moving time-average heart rate signal, and a representation of the supplementary information.

Examples in accordance with a further aspect of the invention provide a computer program product comprising code means configured when executed on a processor to cause the processor to perform the method in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
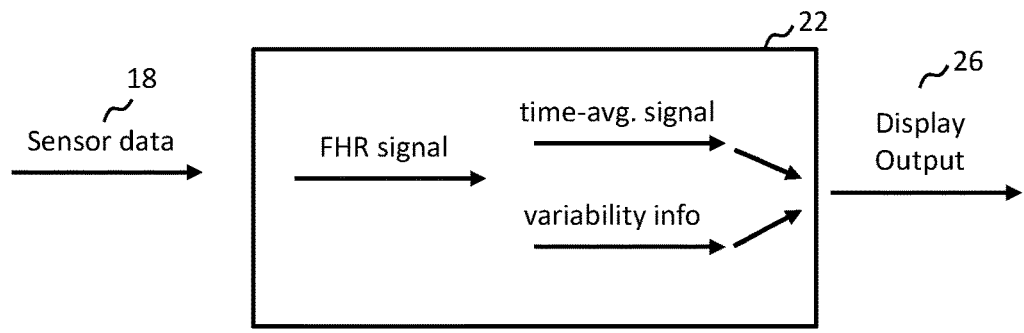
FIG. 1 schematically illustrates an example embodiment of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a device and method for deriving and displaying a time-averaged fetal heart (FHR) rate signal in conjunction with microvariability information relating to variation in the beat-to-beat heart rate signal within the different time-averaging epochs or windows. Thus, supplementary information is displayed, for example temporally aligned or registered with the time-average heart rate signal, which is indicative of variation information for the signal during averaging windows of the time-averaged signal.

When using a FHR system or device, the user interprets the fetal heart rate trace displayed on the display unit based on their prior knowledge and experience. This analysis is essentially a process of pattern matching: matching the patterning of the signal trace to the clinician's memory of previous signal traces and the clinical significance. Therefore in order to ensure timely and reliable interpretation by a clinician, it is preferable for FHR systems to display the fetal heart rate signal trace in a manner that does not deviate from the typical way in which the signal is displayed and presented. For example, it is preferable that the aspect ratio, the recording speed and the appearance of the trace pattern remain substantially the same.

The typical way of presenting the fetal heart rate information is via a time averaged or smoothed fetal heart rate signal trace, in which micro-variability across the defined temporal period is smoothed by averaging over a moving time window of that time period length. Thus, microvariability has in typical previous devices not been displayed or presented. A sudden change in the representation would lead to great difficulties in interpretation.

However, FHR microvariability is a clinically significant parameter for assessing fetal health. Thus, it would be desirable to provide some representational presentation of this information to the user so that they can use it in conjunction with the time average fetal heart rate.

One way would be to simply display the full non-averaged (beat-to-beat) fetal heart rate signal side-by-side with the time average heart rate signal, so that all of the information is presented to the viewer. However this is not a particularly useful or intuitive way of presenting the information, since it is difficult for the clinician to relate the two to one another. Displaying each in a separate graph would for example spatially separate data, despite the fact that the data is part of the same context and hence should be read and interpreted in conjunction.

Embodiments of the present invention thus propose a means for providing information to the user about the fetal heart rate which can include the time average fetal heart rate signal that the clinician is used to interpreting as well as the micro-variability information, presented in a way that allows the two to be easily read in conjunction with one another and interpreted together. For example, ideally the two would be displayed in a way such that they are temporally registered with one another, preferably displayed on the same graph or graph area, for example within the same graph axes.

FIG. 1 schematically outlines the inputs, processing steps, and outputs of an example processing unit or method, for fetal heart rate monitoring, in accordance with one or more embodiments of the invention.

FIG. 1 shows an example processing unit 22. Although the processing unit is illustrated as a single component, in further embodiments it may be implemented by a plurality of processing components, for example a plurality of processors or controllers. Its processing functions may be distributed among a number of processors or components. However, it may be implemented by a single processor, such as a microprocessor unit.

The processing unit is adapted to receive physical sensor data 18 containing information indicative of fetal heart activity and process the sensor data to derive a fetal heart rate signal ("FHR signal"). By way of example, the processing unit may include one or more data input ports for receiving the input sensor data. It may be arranged to receive the input sensor data through a wired or wireless data communication link. The processing unit may have one or more pre-stored algorithms for processing the input data to derive the fetal heart rate signal.

Preferably, the input sensor data is sensor data of sufficient temporal resolution or data sampling rate for the processing unit to derive a beat-to-beat heart rate signal. Thus, preferably the derived heart rate signal is a beat-to-beat heart rate signal. This means a heart rate signal which includes heart rate measurement values for each heart cycle.

The processing unit is further configured to derive a moving time-average signal from the heart rate signal. The time average signal may be computed using a moving time averaging window of a defined duration. The defined duration may be adjustable. It may be consistent across different averaging windows of a given signal or may vary. Preferably it is consistent. The time average-signal provides a smoothed heart rate signal, consistent with the standard presentation of the heart rate signal within standard FHR systems. Thus, clinicians are able to interpret the signal quickly and efficiently using their prior experience and knowledge.

The processing unit is further configured to derive supplementary information based on local variation of the derived heart rate signal during each averaging window of the time-average signal. In this step, the processing unit derives microvariability information about the signal for each of the averaging windows applied in deriving the time average signal. Thus, micro-variability information is derived for each data point of the time average signal, since each data point of the time average signal corresponds to a single averaging window of the full heart rate signal. The supplementary information is preferably indicative of beat-to-beat variability in the heart rate.

The processing unit is further configured to generate a display output 26 for provision to a display device, the display output for simultaneous display of: a graphic representation of a signal trace of the time-average heart rate signal, and a graphic representation of the supplementary information.

The display output may for example be a control signal or control output for controlling a display unit to display the two graphic representations. It may be a data output representative of the desired display presentation of the two graphic representations on the display device, in a data format recognized by the display device.

A graphic representation means pictorial or visual or diagrammatic, as opposed to a text output. The representation may include text (for example labels or associated data values), but should include a graphic or pictorial aspect to the representation of the supplementary information. This makes the displayed information more intuitive to interpret and means that the time-average signal and the supplementary information can be integrated graphically, making it easier to interpret the two in concert.

The graphic representation of the time-average signal includes at least a representation of the signal trace or waveform of the time-average signal.

The graphic representation of the supplementary information may take any of a number of different forms. In some examples, it may also include one or more waveforms of signal traces representative of one or more parameters derived from the variability information. It may take the form of a different type or graph or chart, such as a box chart, a bar chart or graph, a scatter plot or any other example graph or chart. Any other graphical representation may also be used.

The processing unit may be adapted to receive sensor data from any of a number of different sensor modalities. In one set of advantageous embodiments, the processing unit may be adapted to receive ultrasound data, and preferably Doppler ultrasound data. In one other example, the sensor data may include ECG sensor data.

It may receive data directly from one or more sensor units, for example one or more ultrasound probes, or it may receive data from a datastore or a remote server.

There are different options for the supplementary information which is derived from the fetal heart rate signal. In each case, the supplementary information is information related to or based on or representative of a feature or parameter of the variation of the (beat-to-beat) fetal heart rate signal across each averaging or smoothing window.

In some examples, it may comprise a statistical parameter or value derived from the fetal heart rate signal across each averaging window. By way of one selection of non-limiting examples, the supplementary information may include any one or more of: an average heart rate value (e.g. mean, and/or median), a minimum and/or maximum beat-to-beat fetal heart rate across each averaging window, an interquartile range of each averaging window, standard deviation of the heart rate values across each averaging window, percentile ranges for heart rate values across each averaging window, information about outliers in each averaging window, and any other statistics related to fetal heart rate variability within an averaging time interval.

The display output may be configured for displaying the supplementary information and the time-averaged signal in different ways. Preferably, the display output integrates the graphic representation of the supplementary information with the time average heart rate signal in some way, such that the two can be read in conjunction with one another. For example, the supplementary information may be overlaid atop the graphic representation of the time average heart-rate signal, or the graph of the time-average signal may be supplemented or augmented with markings or annotations derived from the microvariability statistics.

For example, the fetal heart rate signal may be displayed as a graph having axes, the axes defining a graph area, and wherein supplementary information is displayed within said same graph area. Preferably the supplementary information is displayed in temporal registration or alignment with the time average heart rate signal. For example, each data point of the supplementary information is displayed temporally registered or aligned with the averaged data point of the time average signal to which it corresponds, i.e. it is aligned with the time point of the particular averaging window to which it corresponds, for example the central time point of the averaging window.

In accordance with one or more embodiments, the supplementary information may be represented in the form of one or more signal traces plotted on the same time axis as the time-average heart rate signal.

The one or more signal traces may for example be spatially offset from the time-average heart rate signal. These supplementary signal traces may in some examples be displayed with a different line style to the line style of the time-average heart rate signal. They may be displayed above or below the time-averaged signal for example. For example, the supplementary signal traces could be plotted with a line style which is fainter, or dashed or dotted, such that it is easily distinguishable from the time average heart rate signal, for example presented on the same time axes.

Figure 2:
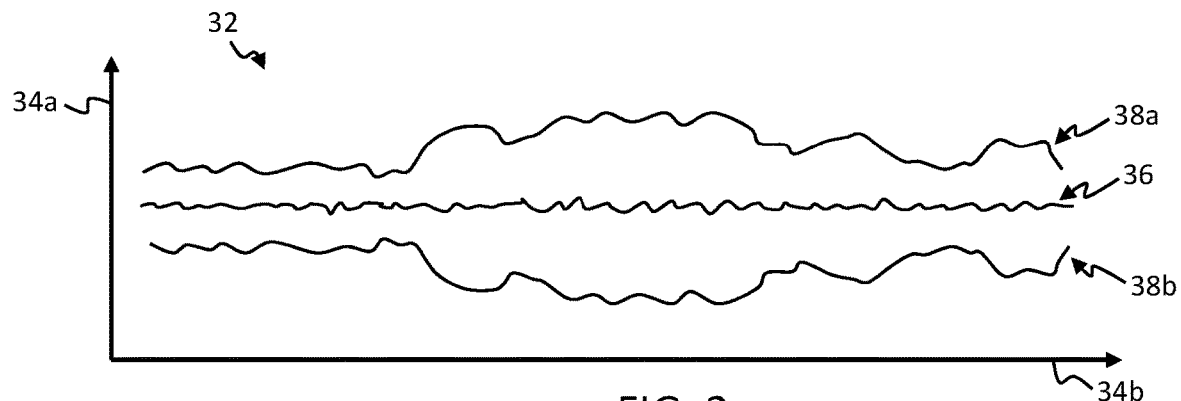
FIG. 2 illustrates an example display output according to one or more embodiments.

FIG. 2 shows one example display output 32 in accordance with one or more embodiments. The display output includes a graphic representation of a signal trace 36 of the time average fetal heart rate signal. The signal trace 36 of the time average heart rate signal is displayed in the form of a graph, having axes 34a, 34b. The x-axis 34b corresponds to time and the y-axis corresponds to heart rate (beats per minute). The x and y axes define a graph area within which the time average heart rate signal trace 36 is rendered.

Displayed on the same graph, within the same graph area is a first supplementary signal trace 38a corresponding to a maximum heart rate value of each averaging window of the time average heart rate signal 36. Also displayed on the same graph, in the same graph area, is a second supplementary signal trace 38 the corresponding to a minimum heart rate value for each averaging window of the time average heart rate signal. The maximum 38a and minimum 38b signal traces are displayed temporally aligned (in temporal registration) with the time-average heart rate signal 36, such that each maximum value of the maximum signal trace 38a, and each minimum value of the minimum signal trace 38b, is aligned with the average heart rate point of the average signal 36 for the same averaging window.

Figure 3:
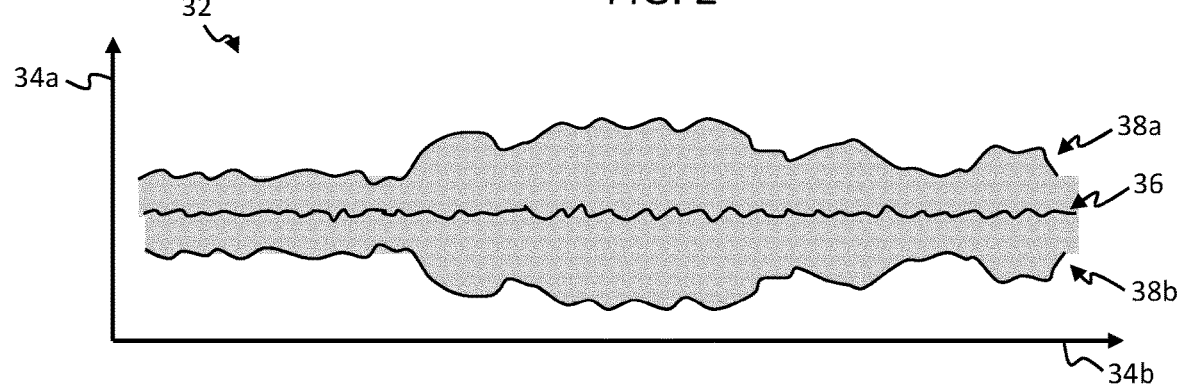
FIG. 3 illustrates a further example display output according to one or more embodiments.

FIG. 3 shows a further example display output 32 in accordance with one or more embodiments. This display output is the same as that of FIG. 2, except that the area between the maximum 38a and minimum 38b signal trace lines is provided shaded or tinted. Although solid shading is shown in FIG. 3, this is by way of example only. It may be crosshatched or highlighted or illuminated or provided a different color or any other form of area fill or highlight marking. By filling or shading the area between the maximum and minimum signal trace lines, this makes the supplementary information (i.e. the maximum and minimum values) easier and more intuitive to interpret in conjunction with the time average heart rate signal 36. It effectively provides a "halo" area around the time-average heart rate signal 36 which enables the supplementary information to be read and interpreted in a highly visual way. Visual presentations of this form are quicker and easier to interpret than for example a text output or simply the signal trace lines alone.

Figure 4:
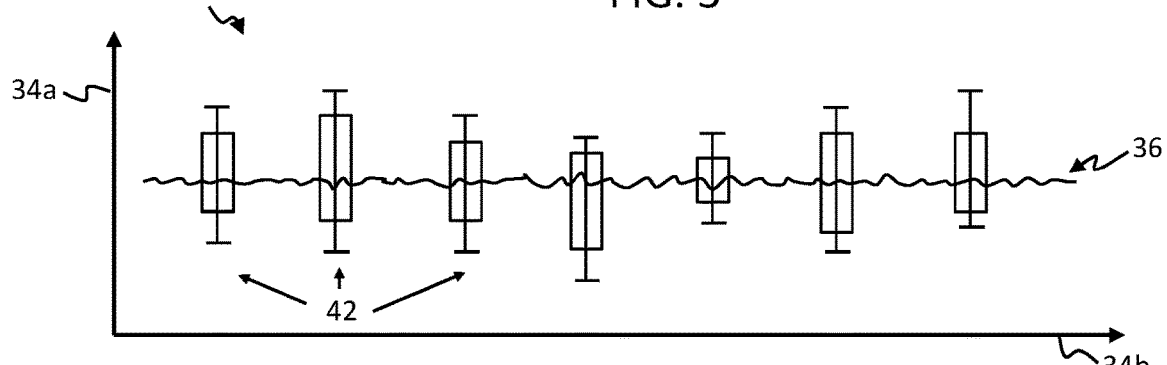
FIG. 4 illustrates a further example display output according to one or more embodiments.

A further example display output 32 in accordance with one or more embodiments is shown in FIG. 4. In this example, the supplementary information is displayed in the form of a series of periodically spaced box plots 42. Each of the box plots is rendered superposed atop the time average heart rate signal 36, temporally aligned with the time point of the time averaging window to which its statistical information corresponds.

Box plot graphs are a well-known and routine graphical representation of statistical information. They may represent at least the maximum and minimum heart rate value for each of the time average windows, and/or a representation of the upper and lower quartiles and the interquartile ranges for each averaging window. Although only a small selection of box plot boxes are shown rendered in FIG. 4, this is by way of ease of illustration only, and in further examples a separate box may be rendered for each time averaging window of the time-average heart rate signal 36.

In accordance with one or more advantageous embodiments, the processing unit may be configured to derive from the time average heart rate signal and/or the supplementary information an assessment of a status of the fetus. It may be configured to derive one or more parameters related to or indicative of fetus status and to further display a representation or indication of these one or more parameters. It may be configured to generate one or more alerts or notifications dependent upon the values of the derived one or more parameters.

The derived information or parameters related to fetal status may include for example whether the fetal heart rate in a pre-defined normal range or is in the bradycardic/tachycardic range. It may include whether arrhythmia is present.

The derived information or parameters related to fetal status may be derived through a combination of averaged heart rate and the supplementary information. For example, tachycardia in combination with high microvariability can indicate early stages of fetal hypoxia.

In one or more examples, the derived information may take into account changes in the heart rate and/or supplementary information over time. For example, tachycardia with increased microvariability occurs in early stages of fetal hypoxia, and is followed by decreasing heart rate with decreasing microvariability if the oxygen supply is not restored. On the other hand, if an episode of tachycardia plus high microvariability is followed by a heart rate in the normal range with normal microvariability, this could be taken as an indication that fetal oxygen supply is sufficient again.

According to one or more embodiments, the derived information may include a prediction of an Apgar score or estimated fetal blood pH or estimated blood lactate content. These estimates can serve as indications as to whether interventions such as performing a C-section are necessary.

Although in embodiments discussed above, the processing unit is configured to generate a display output for causing display of the supplementary information of time-average heart rate signal, in further examples, the processing unit may generate a graphic output for provision to a different output device, for example a printer or projector or a handheld mobile communication device of a user. In all cases, the generated output is an output indicative or representative of the graphic representations of the time-average heart rate signal and the supplementary information. It may be more generally referred to as a graphical output therefore.

Embodiments of the invention include means for processing input sensor data for deriving a fetal heart rate signal. Processes and methods for implementing this step are well known in the field and the skilled person will know of means for deriving a fetal heart rate signal from sensor data from different modalities.

By way of example, a typical method is autocorrelation of the ultrasound signal to determine the short-term period of the signal. The heart rate is the inverse of the short-term period. This method is discussed in U.S. Pat. No. 3,991,365, "Instantaneous frequency measurement system".

Further to this, other methods may also be applied which are also based on detecting short-term periodic components, such as a short-term Fourier transform. Unlike an ECG signal, a Doppler ultrasound signal may not have a clear pattern, as its details depend on what anatomic structures (heart, arteries) are within the ultrasound beam field and on the relative orientation of the structures.

By way of example, from a fetal ECG, the heart rate can be determined by detecting the R waves (or whole QRS complexes) and measuring the time between two R waves, or by other methods that detect short-term periodicity like autocorrelation or Fourier transform. There is a wide variety of methods for detecting R-waves ranging from simple methods such as peak detection, to more complex methods such as use of pattern matching or artificial neural networks.

By way of example, an example method for deriving fetal heart rate from ECG measurement data is outlined in chapter five of "Non-invasive fetal electrocardiogram: analysis and interpretation" by Rik Vullings, or "Detection and Processing Techniques of FECG Signal for Fetal Monitoring" by Hasan et al. (https://www.ncbi.nlm.nih.gov/pmc/articles/PMC3055800/).

Figure 5:
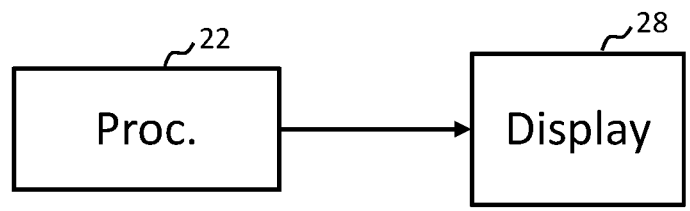
FIG. 5 outlines in block diagram form an example system according to one or more embodiments.

According to a further aspect of the invention, a system can be provided which includes a processing unit in accordance with any example or embodiment outlined above or described below, or in accordance with any claim of this application, and further includes a display unit (or other output device) for displaying the display/graphic output generated by the processing unit. An example is shown in block diagram form in FIG. 5. The display unit 28 is operatively coupled with the processing unit 22.

Figure 6:
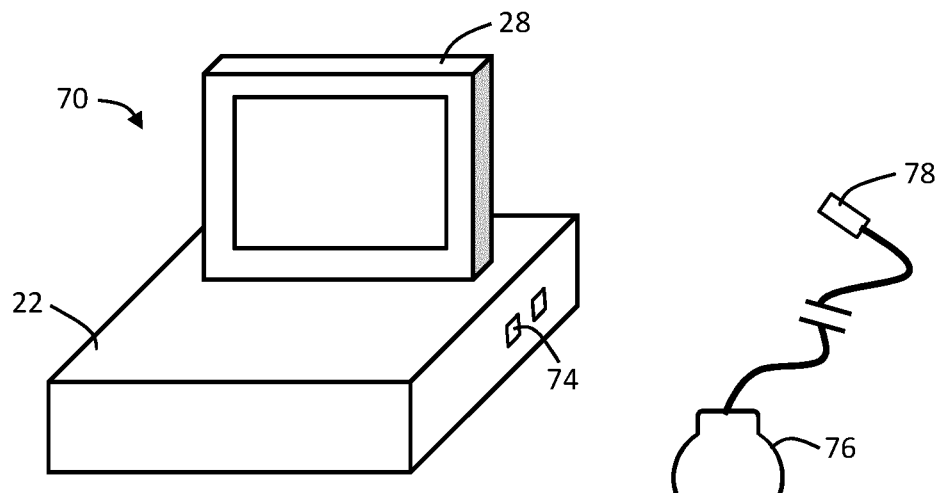
FIG. 6 shows a further example system according to one or more embodiments.

FIG. 6 schematically depicts a further example system 70 in accordance with one or more embodiments. The system includes a processing unit 22 (in this case the system includes a base station which contains one or more processors for performing the function of the processing unit). The system includes a display unit 28 operatively coupled with the processing unit 72. The system in this example further includes a physical sensor unit 76 having a connector 78 for connection in use with an input port 74 of the processing unit. The physical sensor unit is for acquiring physical sensor data for supply to the processing unit. The sensor unit may for example be an ultrasound transducer unit. In other examples it may be an ECG sensor/electrode. In the case of ECG sensing, a plurality of ECG electrodes may be provided for supplying ECG data to the processing unit.

Figure 7:
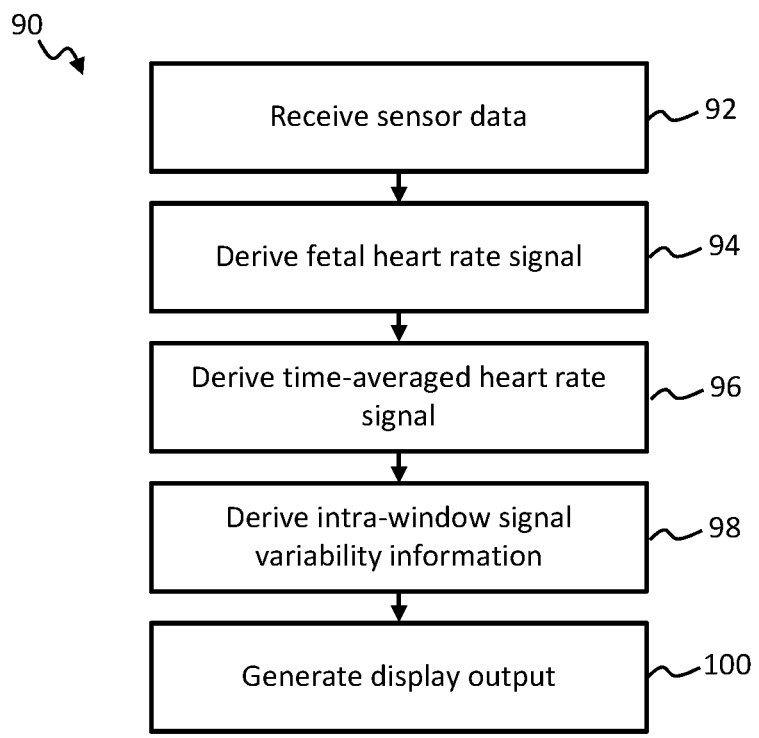
FIG. 7 outlines in block diagram form an example method according to one or more embodiments.

A further aspect of the invention provides a method for use in fetal heart rate monitoring. An example method 90 in accordance with one or more embodiments is outlined in block diagram form in FIG. 7.

The method comprises receiving 92 physical sensor data containing information indicative of fetal heart activity.

The method further comprises processing the sensor data to derive 94 a fetal heart rate signal.

The method further comprises deriving 96 a moving time-average signal from the heart rate signal, with a time averaging window of a defined duration.

The method further comprises deriving 98 supplementary information based on local variation of the heart rate signal during each averaging window of the time-average signal.

The method further comprises generating 100 a display output for provision to a display device, the display output for simultaneous display of: a graphic representation of the time-average heart rate signal, and a representation of the supplementary information.

Implementation options and details for each of the above steps may be understood and interpreted in accordance with the explanations and descriptions provided above for the apparatus aspect of the present invention (i.e. the processing unit aspect).

Any of the examples, options or embodiment features or details described above in respect of the apparatus aspect of this invention (in respect of the processing unit) may be applied or combined or incorporated mutatis mutandis into the present method aspect of the invention.

Examples in accordance with a further aspect of the invention also provide a computer program product comprising computer program code means which, when executed on a computing device having a processing system, cause the processing system to perform all of the steps of the method according to any example method outlined above or in any claim of this application.

As discussed above, the system makes use of processor unit to perform the data processing. The processing unit may include one or more processors. The processor unit can be implemented in numerous ways, with software and/or hardware, to perform the various functions required. The processor unit typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor unit may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A processor configured to:
receive physical sensor data containing information indicative of fetal heart activity and process the physical sensor data to derive a fetal heart rate signal;
derive a moving time-average signal from the fetal heart rate signal, the fetal heart rate signal having a time averaging window of a defined duration;
derive supplementary information for supplementing the moving time-averaged signal additional information about fetal heart rate microvariability based on local variation of the fetal heart rate signal during each averaging window of the moving time-average signal;
generate a display output for provision to a display device, the display output for simultaneous display of: a graphic representation of a signal trace of the moving time-average heart rate signal, and a graphic representation of the supplementary information.

2. The processor as claimed in claim 1, wherein the fetal heart rate signal is displayed as a graph having axes, the axes defining a graph area, and wherein supplementary information is displayed within said same graph area.

3. The processor as claimed in claim 2, wherein the supplementary information is represented in the form of one or more signal traces plotted on the same time axis as the time-average heart rate signal.

4. The processor as claimed in claim 3, wherein the one or more signal traces are spatially offset from the time-average heart rate signal, and optionally displayed with a different line style to the time-average heart rate signal.

5. The processor as claimed in claim 1, wherein the supplementary information includes a minimum and/or maximum fetal heart rate during each averaging window.

6. The processor as claimed in claim 5, wherein the supplementary information includes a first and second signal trace representative respectively of a minimum fetal heart rate and maximum fetal heart rate during each averaging period, the signal traces displayed below and above the time average signal respectively, plotted on the same time axis as the time average signal.

7. The processor as claimed in claim 6, wherein the area between the time average signal and each of the signal traces for the maximum and minimum heart rate values is provided at least partially shaded or colored.

8. The processor as claimed in claim 5, wherein the representation of the supplementary information comprises periodically spaced box plots rendered at successive points along the time-average heart rate signal.

9. The processor as claimed in claim 1, wherein the supplementary information further includes for each of the averaging windows an interquartile range for the heart rate, percentile ranges for the heart rate, and/or a standard deviation of the heart rate.

10. The processor as claimed in claim 1, wherein the physical sensor data is ultrasound data.

11. A system, comprising:
the processor as claimed in claim 1; and
a display device operatively coupled with the processor for receiving the display output.

12. The system as claimed in claim 11, further comprising one or more physical sensors operatively coupled to the processor for supplying the physical sensor data.

13. A processing method comprising:
receiving physical sensor data containing information indicative of fetal heart activity and processing the physical sensor data to derive a fetal heart rate signal;
deriving a moving time-average signal from the fetal heart rate signal, the fetal heart rate signal having a time averaging window of a defined duration;
deriving supplementary information for supplementing the moving time-averaged signal additional information about fetal heart rate microvariability based on local variation of the heart rate signal during each averaging window of the moving time-average signal; and generating a display output for provision to a display device, the display output for simultaneous display of: a graphic representation of the moving time-average heart rate signal, and a representation of the supplementary information.

14. A non-transitory computer readable medium that stores therein a computer program product, which, when executed on a processor, causes the processor to:
receive physical sensor data containing information indicative of fetal heart activity and processing the physical sensor data to derive a fetal heart rate signal;
derive a moving time-average signal from the fetal heart rate signal, the fetal heart rate signal having a time averaging window of a defined duration;
derive supplementary information for supplementing the moving time-averaged signal additional information about fetal heart rate microvariability based on local variation of the heart rate signal during each averaging window of the moving time-average signal; and
generate a display output for provision to a display device, the display output for simultaneous display of: a graphic representation of the moving time-average heart rate signal, and a representation of the supplementary information.

* * * * *